(12) United States Patent
Mathieu et al.

(10) Patent No.: US 10,292,402 B2
(45) Date of Patent: May 21, 2019

(54) METHOD OF SANITIZING EDIBLE SEEDS, PARTICULARLY MUCILAGE PRODUCING SEEDS

(71) Applicant: AGRI-NEO INC., Toronto (CA)

(72) Inventors: Johannes Mathieu, Toronto (CA); Nicholas Dillon, Toronto (CA); Fadi Dagher, Laval (CA); Devin Thomas Michaud, Toronto (CA); Steven Kent Whitesides, Toronto (CA)

(73) Assignee: Agri-Neo Inc., Toronto (CA)

( * ) Notice: Subject to any disclaimer, the term of this patent is extended or adjusted under 35 U.S.C. 154(b) by 0 days.

(21) Appl. No.: 14/940,754

(22) Filed: Nov. 13, 2015

(65) Prior Publication Data

US 2016/0066572 A1    Mar. 10, 2016

Related U.S. Application Data

(63) Continuation-in-part of application No. PCT/CA2014/051088, filed on Nov. 13, 2014.

(60) Provisional application No. 61/907,560, filed on Nov. 22, 2013.

(51) Int. Cl.

| | | |
|---|---|---|
| A01N 25/00 | (2006.01) | |
| A23B 9/26 | (2006.01) | |
| A01N 37/16 | (2006.01) | |
| A23B 9/30 | (2006.01) | |
| A23L 3/3508 | (2006.01) | |
| A23L 3/358 | (2006.01) | |
| A01N 31/02 | (2006.01) | |
| A01N 37/02 | (2006.01) | |
| A23B 9/08 | (2006.01) | |
| A23L 3/3481 | (2006.01) | |

(52) U.S. Cl.
CPC .............. *A23B 9/26* (2013.01); *A01N 25/00* (2013.01); *A01N 31/02* (2013.01); *A01N 37/02* (2013.01); *A01N 37/16* (2013.01); *A23B 9/08* (2013.01); *A23B 9/30* (2013.01); *A23L 3/3481* (2013.01); *A23L 3/3508* (2013.01); *A23L 3/358* (2013.01); *A23V 2002/00* (2013.01)

(58) Field of Classification Search
CPC .................................................... A01N 37/02
USPC .......................................... 424/405; 514/557
See application file for complete search history.

(56) References Cited

U.S. PATENT DOCUMENTS

| | | | |
|---|---|---|---|
| 2,512,640 A | 6/1950 | Greenspan et al. | |
| 2,573,072 A | 10/1951 | Vassel | |
| 2,883,407 A * | 4/1959 | Flenner .................. | C07F 3/106 556/119 |
| 3,330,050 A | 7/1967 | Ausherman | |
| 3,344,533 A | 10/1967 | Peterson | |
| 3,745,669 A | 7/1973 | Meiners | |
| 3,992,147 A | 11/1976 | Christian et al. | |
| 5,849,320 A * | 12/1998 | Turnblad ................ | A01C 1/06 424/410 |
| 6,024,986 A | 2/2000 | Hei | |
| 6,165,483 A | 12/2000 | Hei et al. | |
| 6,238,685 B1 * | 5/2001 | Hei ........................ | A01N 37/16 424/405 |
| 7,291,276 B1 | 11/2007 | Zahn | |
| 7,818,894 B2 | 10/2010 | Noyes et al. | |
| 2002/0197365 A1 | 12/2002 | Kemp et al. | |
| 2003/0211169 A1 | 11/2003 | Tabasso | |
| 2004/0044040 A1 | 3/2004 | Neubert | |
| 2010/0159028 A1 * | 6/2010 | Shultz .................... | A01N 37/16 424/616 |
| 2011/0232181 A1 * | 9/2011 | Kupatt .................... | A01G 7/06 47/58.1 R |
| 2013/0203849 A1 | 8/2013 | Ben | |
| 2013/0216432 A1 | 8/2013 | Lemons | |
| 2013/0259957 A1 | 10/2013 | Dagher et al. | |

FOREIGN PATENT DOCUMENTS

| | | | |
|---|---|---|---|
| CA | 2056503 A1 | 5/1992 | |
| CA | 2569025 A1 | 6/2008 | |
| CA | 2692202 A1 | 3/2009 | |
| CA | 2814794 A1 | 4/2012 | |
| CN | 202274718 U | 6/2012 | |
| CN | 104522161 A | 4/2015 | |
| CN | 104534826 A | 4/2015 | |
| EP | 0648418 B1 | 10/1996 | |
| EP | 0953283 A1 | 11/1999 | |
| FR | 2728171 B1 | 1/1997 | |

(Continued)

OTHER PUBLICATIONS

Agratechniek B.V., "Dehydrated air with adsorption driers", http://uk.agratechniek.nl/drying-with-dehydrated-air-seed.html, accessed Sep. 23, 2015, 8 pages.

(Continued)

*Primary Examiner* — Rei Tsang Shiao

(57) ABSTRACT

Edible seeds are sanitized with a composition comprising water, a biocidal agent and a solvent. The composition is applied to the seeds and the seeds are later dried without first rinsing the seeds. The application rate may be 15% by weight of the seeds or less. The solvent may be a water-miscible alcohol such as ethanol or propylene glycol. When sanitizing mucilaginous seeds, the composition comprises one or more alcohols in an amount effective to inhibit the release of mucilage. The composition is initially applied as a mist to mucilaginous seeds. The biocidal agent may be an oxidizer such as peracetic acid. A treatment system includes an atomizing sprayer and a dryer, for example a fixed bed forced-air dryer.

19 Claims, 4 Drawing Sheets

(56) References Cited

FOREIGN PATENT DOCUMENTS

| GB | 2355198 A | 4/2001 |
|---|---|---|
| WO | 9502330 A1 | 1/1995 |
| WO | 0048469 A2 | 8/2000 |
| WO | 2005060727 A2 | 7/2005 |
| WO | 2007092180 A2 | 8/2007 |
| WO | 2008003779 A1 | 1/2008 |
| WO | 2012051699 A1 | 4/2012 |

OTHER PUBLICATIONS

Agratechniek B.V., "Drying and storage boxes for seed", http://uk.agratechniek.nl/drying-storage-boxes-seed.html, accessed Sep. 23, 2015, 4 pages.

Agratechniek B.V., "Drying installations for seed", http://uk.agratechniek.nl/box-drying-installations-seed.html, accessed Sep. 23, 2015. 8 pages.

Beuchat et al., "Efficacy of Sanitizers in Reducing *Salmonella* on Pecan Nutmeats during Cracking and Shelling," Journal of Food Protection, May 2013, vol. 76 (5), pp. 770-778.

Bucholz et al., "Reduction of *Salmonella* on Alfalfa Seeds using Peroxyacetic Acid and a Commercial Seed Washer is as Effective as Treatment with 20000 ppm of $Ca(Ocl)_2$," Letters in Applied Microbiology, Oct. 2010, vol. 51 (4), pp. 462-468.

European Patent Application No. 14863134, Supplementary European Search Report dated Apr. 20, 2017.

GSI, "Portable Grain Dryers", Jul. 2015.

International Patent Application No. PCT/CA2014/051088, International Preliminary Report on Patentability dated Apr. 20, 2016.

International Patent Application No. PCT/CA2014/051088, International Search Report dated Feb. 5, 2015.

International Patent Application No. PCT/CA2014/051088, Written Opinion dated Feb. 5, 2015.

International Patent Application No. PCT/CA2015/051187, International Search Report and Written Opinion dated Jan. 27, 2016.

Mena et al., "Influence of Ethanol on Probiotic and Culture Bacteria Lactobacillus Bulgaricus and *Streptococcus thermophiles* within a Therapeutic Product," Open Journal of Medical Microbiology, 2012, vol. 2 (3), pp. 70-76.

Montville et al., "Analysis of Published Sprout Seed Sanitization Studies Shows Treatments are Highly Variable," Journal of Food Protection, Aug. 2003, vol. 67 (4), pp. 758-765.

Naewbanij et al. Mycotoxin prevention and control in foodgrains—Batch and Continuous drying, http://www.fao.org/docrep/x5036e/x5036e0x.htm, accessed Sep. 23, 2015.

North Dakota State University, Grain Drying, Oct. 2013.

Pao et al., "Utilizing Acidic Sprays for Eliminating *Salmonella enterica* on Raw Almonds," Journal of Food Science, Jan. 2006, vol. 71 (1), pp. M14-M19.

Rice Knowledge Bank, "Fixed bed batch dryer", http://www.knowledgebank.irri.org/index.php?option=com_zoo&task=item&item_id=11368,Itemid=820, accessed Sep. 23, 2015.

Rice Knowledge Bank, "Options for Heated air drying", http://www.knowledgebank.irri.org/training/fact-sheets/postharvest-management/drying-fact-sheet-category/options-for-heated-air-drying-fact-sheet?tmpl=component&print=1, accessed Sep. 23, 2015.

Rice Knowledge Bank, "Vietnamese low cost SRR dryer", http://www.knowledgebank.irri.org/index.php?option=com_zoo&task=item&item_id=11418,Itemid=820, accessed Sep. 23, 2015.

Smith et al., "Microbial Synergy via an Ethanol-Triggered Pathway," Molecular and Cellular Biology, May 2004, vol. 24 (9), pp. 3874-3884.

Trinetta, et al., "Chlorine Dioxide for Microbial Decontamination of Food," Microbial Decontamination in the Food Industry: Novel Methods and Applications, 2012, pp. 533-562.

Weissinger et al., "Comparison of Aqueous Chemical Treatments to Eliminate *Salmonella* on Alfalfa Seeds," Journal of Food Protection, Nov. 2000, vol. 63 (11), pp. 1475-1482.

NOSB TAP Materials database compiled by OMRI, Nov. 3, 2000. 7 pages.

Divekar, Varsha B., "Isolation and Characterization of Mucilage from Lepidium Sativum Linn. seeds", International Journal of Pharma. Research & Development—Online, Issue 1, Mar. 2006. 5 pages.

Ding et al., "Germicidal Efficacy of Sanitizers on Food-Borne Bacteria and Effect of Sanitizes in CIP and SIP Simulation," European Food Research and Technology, Aug. 2013, vol. 237 (2), pp. 265-274.

European Patent Application No. 14863134.4, Office Action dated May 31, 2018.

European Patent Application No. 15859463.0, Extended European Search Report dated Mar. 29, 2018.

U.S. Appl. No. 15/038,211, Non-Final Office Action dated Jun. 25, 2018.

U.S. Appl. No. 15/515,678, Non-Final Office Action dated Jan. 10, 2018.

Australian Patent Application No. 2014353838, Notice of Acceptance dated Sep. 3, 2018.

Australian Patent Application No. 2014353838, Exam Report No. 2 dated Jul. 25, 2018.

Australian Patent Application No. 2014353838, Exam Report No. 1 dated Sep. 19, 2017.

U.S. Appl. No. 15/515,678, Final Office Action dated Feb. 21, 2019.

Australian Patent Application No. 2015345924, Examination Report dated Mar. 1, 2019.

European Patent Application No. 14863134.4, Examination Report dated Mar. 6, 2019.

\* cited by examiner

METHOD OF SANITIZING EDIBLE SEEDS, PARTICULARLY MUCILAGE PRODUCING SEEDS

RELATED APPLICATIONS

This application claims priority from, and for the U.S.A. is also a continuation-in-part of, International Application Number PCT/CA2014/051088, A Novel Composition and Method of Use to Control Pathogens and Prevent Diseases in Seeds, filed on Nov. 13, 2014 by Agri-Neo Inc., which is incorporated by reference.

FIELD OF THE INVENTION

The invention relates to the preservation of edible seeds, including sprouted seeds.

BACKGROUND

Seeds, such as flax, chia, hemp and sesame seeds, are economically valuable and nutritious food products. However, there are many potential points of entry for pathogens in the seed processing chain between harvesting and packaging. Some pasteurized seeds are commercially available. However, pasteurizing cooks the seeds and is not an option for seeds that are marketed as raw. The seeds are believed to have more nutritional value when raw, and raw seeds are at preferred by at least some consumers.

Some raw fruits and vegetables have been sanitized with aqueous compositions. For example, U.S. Pat. No. 2,512,640 describes the use of peracetic acid (also known under the tradename Peracid) for the treatment of raw fruits and vegetables to reduce spoilage from bacteria and fungi before processing. Peracetic aqueous solutions have also been suggested to control pathogenic organisms on growing plants (International Patent Publication WO 2012/051699 and U.S. Pat. Nos. 6,024,986; 6,165,483; and, 6,238,685).

As a consequence of their small size, however, seeds have a much larger surface area for a given volume than most fruits and vegetables. Aqueous sanitizing solutions generally employ a contact killing mechanism and so efficacy depends on coverage. This suggests that a large volume of any aqueous composition would be required to treat seeds, but seeds are typically stored and processed dry.

Some seeds also release mucilage when wet. Mucilage is a polysaccharide with a high swelling index that produces a viscous solution in water. Mucilaginous seeds contain mucilage-secreting cells (MSCs) primarily located in the seed coat, or epidermal layer of the seed. When the seeds are dry, the mucilage is contained in cell wall structures, for example between primary and secondary cells walls. When the seeds contact water, the mucilage swells, breaks free of the cell structures, and covers the seeds with mucilage. The mucilage is edible but, if secreted, it binds the seeds together making the seeds difficult to process and store. Examples of commercially important mucilage producing seeds include flax and chia.

Current food safety practices for raw seeds rely on sampling. When sampling detects an excess of pathogens, large containers of seed are wasted. And yet sampling also fails to detect all contaminated shipments. For example, sesame, chia and flax seeds have all caused outbreaks of Salmonella poisoning among people eating the raw seeds.

INTRODUCTION TO THE INVENTION

This specification describes a system and method for sanitizing raw edible seeds with an aqueous composition. The system and method can be used to provide preventative sanitization, or to sanitize seeds that already have an unacceptable pathogen concentration. The seeds may be whole, or in alternative forms such as sprouted, cracked or powdered.

The method involves applying an aqueous sanitizing composition to the seeds. The composition includes at least one biocidal agent and at least one solvent. Preferably, the solvent is a water-miscible alcohol that is food-grade, volatile, or both. Some examples of suitable solvents include ethanol and propylene glycol. The biocidal agent may be an oxidizer such as peracetic acid.

The composition is applied sparingly to the surface of the seeds. For example, the application rate may be 15% by weight of the seeds or less. Sufficient sanitizing may occur essentially on initial contact, or within about 5 minutes, but contact time may be extended to further reduce the number of living pathogens on the seeds. However, the seeds are dried no more than 48 hours, preferably no more than 24 hours, after applying the composition. Drying returns the seeds to a moisture content suitable for storing the seeds, and preferably vaporizes at least most of the solvent and optionally the biocidal agent. The seeds are not rinsed before they are dried. The seeds can be dried, for example, by blowing air over them.

The method may be used for sanitizing mucilaginous seeds, such as chia and flax seeds. In this case, the aqueous sanitizing composition is prepared with an alcohol, or a mixture of alcohols, in an amount effective to suppress mucilage release from the seeds. For example, the composition may comprise at least 15% v/v ethanol, or at least 13% v/v propylene glycol. The composition is initially applied to the mucilaginous seeds as a mist. The composition sanitizes the seeds without causing mucilage production.

The system includes equipment adapted to perform the method. Preferred application equipment has one or more atomizing sprayers, optionally with a downstream mixer. Preferred drying equipment includes a fixed bed dryer with forced-air flow through the bed.

DETAILED DESCRIPTION

Figure 1:
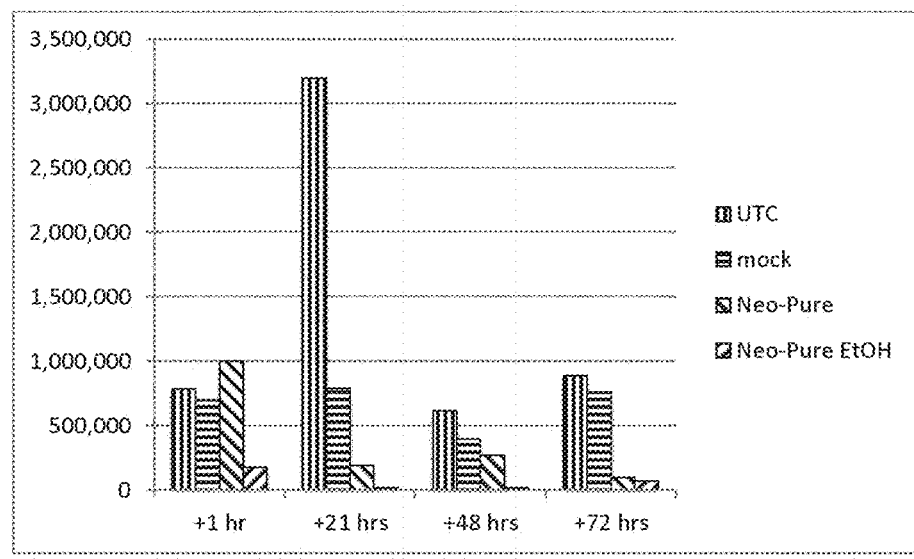
FIGS. 1 to 3 represent results obtained according to Example 2.

Popular raw edible seeds include hemp, flax, sesame and chia seeds. Raw seeds can be eaten whole, sprouted, cracked or as a powder. The description below describes an aqueous sanitizer composition, which may be referred to as a sanitizer or composition for brevity. The sanitizer can be used to kill disease-causing pathogens such as viruses, bacteria, fungi, yeasts and molds. Common bacterial pathogens include *Salmonella, Listeria monocytogenes* and *E. coli*. The sanitizer may be used, for example, to control *E. coli* in hemp seeds and *Salmonella* in chia seeds. The sanitizer is typically used after the seeds have been harvested and before they are packaged. The sanitizer may be used as a preventative treatment, or after an unacceptable contamination has been detected.

Seeds are difficult to treat with an aqueous sanitizer composition because they are small, and have a very high surface area per unit volume. Since seeds are also generally stored and processed in a dry state, it is preferable not to apply a large volume of the sanitizer. Some seeds also release mucilage when they contact water. In the method described below, an aqueous sanitizer includes one or more biocidal agents and one or more solvents. The solvent is believed to help disperse the composition across the seed. Applying the composition as a mist also helps disperse the compositions, and is particularly useful for treating mucilaginous seeds. The composition can be effective even at low application rates, for example 15 wt % (150 L/tonne) or less or 5 wt % (50 L/tonne) or less. After applying the composition, the seeds are dried typically to or near their original moisture content, for example within 1% by weight of the seeds of their original moisture content. This inhibits regrowth of microorganisms and, preferably, vaporizes the solvent and possibly the biocidal agent. The seeds do not need to be rinsed of the composition.

The term "solvent" is used as in the chemical engineering vernacular to mean an organic liquid capable of dissolving a variety of compounds. The solvent should be miscible in water, at least to some concentration. The solvent is preferably volatile or food grade or both. Ideally, the solvent should be generally regarded as safe (GRAS) according to any relevant law dealing with the production or sale of food in the relevant jurisdiction. To enable larger amounts of solvent to be used, the solvent may be a hydroxylated hydrocarbon, i.e. an alcohol. Examples of useful solvents include alcohols such as ethanol and propylene glycol. Other potentially useful solvents include glycol ethers, ethylene glycol, isopropanol, and monobutyl ether of ethylene glycol. The solvent may represent from 2-70% by volume, preferably 50% or less by volume, optionally less than 20% by volume, but preferably at least 15% by volume, of the total volume of the composition.

In general, lower alcohols are useful solvents because of their miscibility in water. For example, the solvent may be selected from the group consisting of $C_1$-$C_6$ alcohols and glycol ethers. In particular, the solvent may be an alcohol of formula ROH where R represents a linear alkyl group having from 1 to 6 carbon atoms, or a branched alkyl group having from 3 to 6 carbon atoms. The alcohol may also be a food-grade alcohol that is listed in FDA's CFR 21 as Generally Regarded as Safe (GRAS) for use in food (section 184.1293), such as ethanol, propanol or isopropanol.

Alcohol solvents, and possibly some others, also allow the composition to be applied to mucilaginous seeds without causing them to express material amounts of mucilage. The reason why alcohols suppress mucilage release when added to the composition is unknown. Without intending to be limited by theory, the inventors believe that the effect may be a result of a change in polarity of the composition relative to water. Alternatively, the effect may be related to the way that an alcohol causes DNA, for example, to precipitate out of solution with water, although the amount of alcohol required to inhibit mucilage release is much lower.

The effective amount required to suppress mucilage release varies slightly between different alcohols, but can be easily determined by trials at different concentrations. The effective amount for ethanol is a concentration of about 15% by volume. The effective amount for propylene glycol is a concentration of about 13% by volume. The effective amount of a 50:50 mixture of propylene glycol and ethanol is a concentration of about 14% by volume. Effective amounts for other mixes of ethanol and propylene glycol can be obtained by linear interpolation of theses results. Alternatively, since ethanol is a light, low alcohol yet the effective amount for propylene glycol (a diol of higher density) is not markedly different, these results suggest that about 15% by volume is likely to be effective for any alcohol or mixture of alcohols. The effective amount appears to be related to the concentration of the alcohol independent of the application rate of the alcohol.

Higher solvent concentrations may also be used. Concentrations of up to 50% ethanol have been tested and found effective. Ethanol at a 15% concentration is generally biostatic, it does not cause significant growth or death of most pathogens. Ethanol at 50% concentration increases the biocidal effect of the sanitizing composition. However, the increased biocidal effect is most significant with short contact times, for example about 3 to 12 hours between initial application and drying the seeds. With longer contact times, the increase in biocidal effect attributable to the ethanol decreases. For example, in tests on hemp seeds an increase in contact time from 12 hours to 24 hours was found to be more effective than adding 50% ethanol, both cases being relative to a formulation without ethanol applied for 12 hours. Depending on the practical circumstances of any particular plant, this observation may indicate (a) that efficacy can be obtained without increasing solvent concentration by extending the contact time or (b) that efficacy can be obtained with a short contact time by increasing solvent concentration.

Some solvents are also difficult to handle at high concentration. For example, an aqueous mixture containing ethanol at more than 20% by volume is considered flammable while a mixture with 20% or less ethanol is considered combustible. Combustible materials are safer and have fewer handling requirements. Accordingly, a solvent concentration of 20% by volume or less may be preferred in some cases. An ordinary mixer can be used to prepare sanitizer compositions with 20% or less ethanol.

Even with a solvent, treatment of mucilaginous seeds in particular is sensitive to the initial application of the composition. It is preferable to disperse the composition and provide a large initial contact area rather than to rely on mixing after initial application to disperse the composition. For example, applying the composition through an atomizer to produce a mist improves the efficacy of the treatment over applying the composition in a continuous spray. The composition can be applied as an atomized spray to the seeds or the seeds can fall though a mist of the composition. In one example in which a continuous spray was used to initially apply a composition to chia seeds, mucilage did not form but the microbial kill was not effective. However, the chia seeds were effectively sanitized when a similar composition was applied with an atomized spray.

Agricultural seed treatment equipment, normally used to apply an antimicrobial or fungicidal chemical to seeds before planting them, or modifications thereof, can be used. For non-mucilaginous seeds, the initial application is less critical and an ordinary sprayer may be used, followed by secondary mixing. Secondary mixing is also useful even when the composition is applied as a mist and can be performed, for example, in an auger, tumbler or rotating drum. Agricultural seed treating equipment may provide both initial application and secondary mixing. Suitable equipment includes the USC Continuous Treating System, Bayer RH series treaters, USC LPX series treaters and the KSi 4808NGA applicator.

The biocidal agent in the composition may be any one or more biocidal agents in amounts effective to sanitize seeds to a level safe for human consumption. Suitable oxidants include peracetic acid, hydrogen peroxide, iodine, chlorine, bromine and chlorine dioxide. A mixture of two or more oxidants may also be used. The one or more oxidants may be present in a weight ratio ranging from 1:100 to 1:4, for example 1:20 to 1:5, relative to the water. Optionally, the composition may include a surfactant.

Peracetic acid ($C_2H_4O_3$) is particularly useful because it effectively kills on contact and essentially vaporizes when the seeds are dried. Paracetic acid can be obtained as a liquid preformed product or generated in-situ from powder precursors. Peracetic acid in an aqueous solution is a mixture comprising acetic acid ($CH_3COOH$) and hydrogen peroxide ($H_2O_2$). Typically, peracetic acid (also identified hereinafter under the acronym PAA) is produced by reacting acetic acid and hydrogen peroxide. Methods of generating a liquid solution comprising PAA starting from the dissolution of a powdered mixture are described in U.S. Pat. No. 7,291,276; UK patent application No. 2,355,198; FR patent application 2,728,171; Canadian patent application No. 2,569,025; International PCT patent application WO 95/02330 and EP patent application No. 0 648 418, which are incorporated by reference.

The treatment process, in summary, includes providing a sanitizing composition having a solvent and a biocidal agent mixed with water. This composition is applied to the seeds. The application rate is preferably less than 15% by weight of the seeds, typically 3-5% (30-50 L/tonne). Optionally, there may be secondary mixing after the initial application. Sufficient sanitizing may occur essentially on initial application, or in the time taken for secondary mixing and transport to a dryer, for example in about 5 minutes. Optionally, the seeds may be stored after initial application for an hour or more with the composition in contact with the seeds. The seeds are dried to end the process. Drying continues until the seeds return to or near their starting moisture content, or at least until the seeds are below a moisture content, for example 10 wt %, suitable for storing them. The seeds do not need to be rinsed before they are dried, and mucilaginous seeds in particular are not rinsed.

To store the seeds in contact with the composition, the seeds can be conveyed into solid (non-porous) storage bins. The bins are preferably covered, but not airtight. Some of the solvent may evaporate during the contact time, and it is preferable to allow the solvent to escape to avoid having a flammable gas over the seeds. In one trial, seeds were treated with a 50% ethanol composition and stored in a conventional covered agricultural grain bin. There was no detectable ethanol in air in the bin when measured 16 hours after adding the seeds.

The seeds can be dried in a fixed or moving bed by sucking or blowing hot air through the bed. The air is heated, primarily to increase the ability of the air to hold water. This allows the air to dry the seeds even if the air is initially saturated. Alternatively or additionally, the air may be dehumidified before it passes through the bed of seeds. However, the air should not be heated to an extent that would render the seeds no longer raw. Different standards exist for marketing raw seeds, and the maximum temperature may be in the range of 37-70° C., typically 40-49° C. For example, the air may be heated to not more than 40° C. The seeds can be dried in agricultural grain driers or in fixed bed batch driers. Fixed bed batch driers are preferred since they produce less dust and seed damage. The drier can be, for example, a circular bin dryer with air supplied to a vertically oriented central porous tube inside of a cylindrical bin holding the seeds. The cylindrical bin has a solid bottom and porous sides. A floating solid cover can be used to allow for the bed to contract as it dries. Optionally, an outside-in airflow path may be used to provide increased air velocity across the downstream seeds. In another option, frusto-conical central tube or outer bin walls can be used to provide more nearly equal airflow through the top and bottom of the bed. Alternatively, commercial rectangular drying boxes can be used, optionally to both hold the seeds during a contact time and while drying the seeds.

Example #1 Protocols for Seeds, Drains and Spices Sanitation

I—Preparation of Different Solutions
  1. Wetting Agent (i.e. Surfactant) Preparation:
  Description:
  APG® 325 is a liquid wetting agent (i.e. a surfactant) composed of alkyl polyglycoside and derived from natural sources. It is a foaming surfactant.
  Preparation:
  5 g of liquid APG 325 surfactant were diluted in 1 L water, and mixed for 5 minutes, to make 0.5% solution of wetting agent (i.e. surfactant).
  2. Alcohol Preparation:
  Description:
  A food-grade alcohol based on ethanol at 94% concentration minimum (provided by Greenfield Ethanol).
  Preparation:
  100 ml of the above-mentioned ethanol were diluted in 100 ml water to a make a 50% food grade ethanol.
  3. Powdered Peracetic Acid Preparation without Surfactant:
  Description:
  A blend of sodium percarbonate (62% w/w), TAED (20% w/w) and citric acid (18% w/w) that generates peracetic acid and hydrogen peroxide in-situ. It is a non-foaming solution and free of surface-active agents. This Powdered PAA is equivalent to 10% peracetic acid.
  Preparation:
  100 g of Powdered PAA was dissolved in 1 L water and mixed for 10-15 min until peracetic acid is generated in-situ. Both peracetic acid and hydrogen peroxide can be tested via Lamotte test kit code 7191-02. This solution was to be used within 6 hours to maintain a high concentration of peracetic acid.
  4. Neo Pure Preparation:
  Description:
  Neo Pure is a powdered composition that generates peracetic acid in-situ via TAED, sodium percarbonate and citric acid mixture. Also, it generates hydrogen peroxide and contains a poylglycoside wetting agent (i.e. a surfactant).

Neo Pure is equivalent to 10% peracetic acid. More particularly, the Neo Pure had the following formulation:

| | |
|---|---|
| Sodium percarbonate | 58% w/w |
| Tetraacetylethylenediamine (TAED) | 20% w/w |
| Citric acid (food-grade) | 18% w/w |
| Glucopon 50 G surfactant (alkylpolyglycoside) | 4% w/w |
| Total | 100% |

Preparation:
100 g of Neo Pure was dissolved in 1 L water and mixed for 10-15 min until peracetic acid was generated in-situ. Both peracetic acid and hydrogen peroxide can be tested via Lamotte test kit code 7191-02. This solution was to be used within 6 hours to maintain a high concentration of peracetic acid.

5. Neo Pure Preparation with Alcohol:
Description:
Neo Pure is a powdered composition that generates peracetic acid in-situ via TAED, sodium percarbonate and citric acid mixture. Also it generates hydrogen peroxide and contains a poylglycoside wetting agent (i.e. a surfactant). Neo Pure is equivalent to 10% peracetic acid.
Preparation:
100 g of Neo Pure were dissolved in 1 L water and mixed for 10-15 min until peracetic acid was generated in-situ. Then, 100 ml of the solution so obtained was mixed with 100 ml ethanol 94% for 10 minutes.

6. Liquid Peracetic Acid Preparation without Wetting Agent:
Description;
PERCID is a CFIA approved liquid preformed peracetic acid. PERCID is a concentrated 5% peracetic acid formula composed of mixing liquid acetic acid with liquid hydrogen peroxide.
Preparation:
200 ml of PERCID was dissolved in 1 L water and mixed for 5 minutes. A non-foaming solution free of surface-active agents such as a wetting agent, was obtained.

7. Liquid Peracetic Acid Preparation with a Wetting Agent (i.e. a Surfactant):
Description:
PERCID is a CFIA approved liquid preformed peracetic acid. Percid is a concentrated 5% peracetic acid formula composed of mixing liquid acetic acid with liquid hydrogen peroxide. PERCID solution is mixed a liquid wetting agent (i.e. surfactant) APG 325.
Preparation:
200 ml of PERCID was dissolved in 1 L water and mixed for 5 minutes. Then, 5 g of APG® 325 was added to the solution so obtained, and mixed for 5 minutes. A foaming PAA solution was obtained.

8. Liquid Peracetic Acid Preparation with Wetting Agent (i.e. Surfactant) and Alcohol:
Description:
PERCID is a CFIA approved liquid preformed peracetic acid. PERCID is a concentrated 5% peracetic acid formula composed of mixing liquid acetic acid with liquid hydrogen peroxide. PERCID solution is mixed a liquid wetting agent (i.e. surfactant) APG® 325.
Preparation:
200 ml of PERCID was dissolved in 1 L water, and mixed for 5 minutes. Then, 5 g of APG® 325 were added to the resulting solution, and mixed for 5 minutes. A foaming PAA solution was obtained. Then, 100 ml of this foaming PAA was mixed with 100 ml ethanol 94% for 10 minutes, to provide the liquid peracetic acid preparation with wetting agent and alcohol.

9. Powdered Peracetic Acid Preparation with Alcohol:
Description:
A blend of sodium percarbonate (62%), TAED (20%) and citric acid (18%) that generates peracetic acid and hydrogen peroxide in-situ. It is a non-foaming solution and free of surface active agents. This powdered PAA is equivalent to 10% peracetic acid.
Preparation:
100 g of Powdered PAA were dissolved in 1 L water, and mixed for 10-15 min until peracetic acid is generated in-situ. Then, 100 ml of the solution so obtained was mixed with 100 ml ethanol 94% for 10 minutes.

10. Liquid Peracetic Acid Preparation with Alcohol:
Description:
PERCID is a CFIA approved liquid preformed peracetic acid. PERCID is a concentrated 5% peracetic acid formula composed of mixing liquid acetic acid with liquid hydrogen peroxide.
Preparation:
200 ml of PERCID were dissolved in 1 L water, and mixed for 5 minutes. A non-foaming PAA solution was obtained. Then, 100 ml of this non-foaming PAA was mixed with 100 ml Ethanol 94% for 10 minutes, to provide the liquid peracetic acid preparation with alcohol.

II—Preparation of Different Seeds Grains.

Seeds were mechanically cleaned and spread in stainless steel containers. Each 100 grams seeds were sprayed with 4 ml total solutions descried above via conventional trigger vaporizer. This solution is equivalent to 40 L disinfecting solution total sprayed on 1-tonne seeds. Seeds, grains and spices were selected to represent all families and types of seeds, grains and spices. Another criterium was to select seeds and grains contaminated with a high count of total aerobic bacteria, yeast, mold, *E. coli, Salmonella* sp. and other pathogenic microorganisms.

Seeds, grains and spices treated were:
Whole dried pea,
Split pea dried,
Pea fiber,
Vanilla,
Chia,
Sprouted flax and chia,
Flax,
Hemp, and
Black pepper seeds

TABLE 1

| | III- RESULTS on whole dried pea | | |
|---|---|---|---|
| Treatments | Total count Aerobic - CFU/g bacteria | Physical Characteristics | Organoleptic |
| 0- Untreated | Av = 800,000<br>n1 = 700,000<br>n2 = 890,000<br>Av = 1,000 Y&M<br>n1 = 1000/n2 = 1000 | No effect | No effect |
| 1- Wetting agent APG 325<br>0.5% | Av = 925,000<br>n1 = 850,000<br>n2 = 1 million<br>Av = 1,000 Y&M<br>n1 = 1000/n2 = 1000 | No effect | No effect |
| 2- Alcohol - ethanol<br>50% | Av = 900,000<br>n1 = 800,000<br>n2 = 1 million<br>Y&M not detected<br>n1, n2 not detected | No effect | No effect |
| 3- Powdered PAA Alone<br>4 kg/40 L | Av = 300,000<br>n1 = 250,000<br>n2 = 350,000<br>Y&M not detected<br>n1, n2 not detected | No effect | No effect |
| 4- Neo Pure<br>4 kg/40 L | Av = 150,000<br>n1 = 170,000<br>n2 = 130,000<br>Y&M not detected<br>n1, n2 not detected | No effect | No effect |
| 5- Neo Pure + alcohol<br>2 kg/20 L + 20 L | Av = 60,000<br>n1 = 60,000<br>n2 = 60,000<br>Y&M not detected<br>n1, n2 not detected | No effect | No effect |
| 6- Percid -Liquid PAA alone<br>8 L/40 L | Av = 250,000<br>n1 = 230,000<br>n2 = 270,000<br>Y&M not detected<br>n1, n2 not detected | No effect | No effect |
| 7- Percid -Liquid PAA<br>8 L/40 L + wetting agent | Av = 50,000<br>n1 = 80,000<br>n2 = 20,000<br>Y&M not detected<br>n1, n2 not detected | No effect | No effect |
| 8- Percid -Liquid PAA +<br>wetting agent + alcohol (94%)<br>4 L/20 L + 20 L ethanol +<br>wetting agent | Av = 5,000<br>n1 = 5,000<br>n2 = 5,000<br>Y&M not detected<br>n1, n2 not detected | No effect | No effect |
| 9- Powdered PAA +<br>alcohol (94%)<br>2 kg/20 L + 20 L ethanol | Av = 70,000<br>n1 = 85,000<br>n2 = 55,000<br>Y&M not detected<br>n1, n2 not detected | No effect | No effect |
| 10- Percid -Liquid PAA +<br>alcohol<br>4 L/20 L + 20 L ethanol<br>(94%) | Av = 60,000<br>n1 = 80,000<br>n2 = 40,000<br>Y&M not detected<br>n1, n2 not detected | No effect | No effect |

Conclusion:

The polyglycoside wetting agent (i.e. surfactant) was not bactericidal and can act as a food source for the bacteria Alcohol (50% concentration) applied at ratio of 40 L per 1 tonne peas was not a strong bactericidal agent.

Peracetic acid either preformed via liquid formulations or in-situ generated via powdered formulations, showed to be a strong bactericidal agent and reduced the level of bacteria, yeast and mold significantly.

Wetting agent (i.e. surfactant) combined to peracetic acid formulations increased the efficiency of the oxidizer and showed to be synergistic with peracetic acid.

Alcohol (ethanol) combined with peracetic acid formulations increased the efficiency of the oxidizer and showed to be synergistic with peracetic acid.

Both alcohol and wetting agent (i.e. surfactant) increase the coverage of peracetic acid and help this limited amount of solution (40 L per 1 tonne seed) to better cover the seeds and penetrate the seeds and target microorganisms. They showed a synergistic effect that is higher than the one of the peracetic acid with a wetting agent or the peracetic acid with an alcohol.

TABLE 2

| Treatments | Total count Aerobic CFU/g bacteria | Physical Characteristics | Organoleptic |
|---|---|---|---|
| IV- RESULTS on whole split pea | | | |
| 0- Untreated | Av = 800,000<br>n1 = 750,000<br>n2 = 850,000<br>Av = 1,000 Y&M<br>n1 = 1000/n2 = 1000 | No effect | No effect |
| 1- Wetting agent APG 325 0.5% | Av = 900,000<br>n1 = 930,000<br>n2 = 870,000<br>Av = 1,000 Y&M<br>n1 = 1000/n2 = 1000 | No effect | No effect |
| 2- Alcohol - ethanol 50% | Av = 700,000<br>n1 = 700,000<br>n2 = 700,000<br>Y&M not detected<br>n1, n2 not detected | No effect | No effect |
| 3- Powdered PAA Alone 4 kg/40 L | Av = 400,000<br>n1 = 430,000<br>n2 = 370,000<br>Y&M not detected<br>n1, n2 not detected | No effect | No effect |
| 4- Neo Pure 4 kg/40 L | Av = 350,000<br>n1 = 450,000<br>n2 = 250,000<br>Y&M not detected<br>n1, n2 not detected | No effect | No effect |
| 5- Neo Pure + alcohol 2 kg/20 L + 20 L ethanol (94%) | Av = 100,000<br>n1 = 80,000<br>n2 = 120,000<br>Y&M not detected<br>n1, n2 not detected | No effect | No effect |
| 6- Percid -Liquid PAA alone 8 L/40 L | Av = 300,000<br>n1 = 400,000<br>n2 = 200,000<br>Y&M not detected<br>n1, n2 not detected | No effect | No effect |
| 7- Percid -Liquid PAA 8 L/40 L + wetting agent | Av = 200,000<br>n1 = 200,000<br>n2 = 200,000<br>Y&M not detected<br>n1, n2 not detected | No effect | No effect |
| 8- Percid -Liquid PAA + wetting agent + alcohol (94%) 4 L/20 L + 20 L ethanol + wetting agent | Av = 50,000<br>n1 = 80,000<br>n2 = 30,000<br>Y&M not detected<br>n1, n2 not detected | No effect | No effect |
| 9- Powdered PAA + alcohol (94%) 2 kg/20 L + 20 L ethanol | Av = 150,000<br>n1 = 200,000<br>n2 = 100,000<br>Y&M not detected<br>n1, n2 not detected | No effect | No effect |
| 10- Percid -Liquid PAA + alcohol 4 L/20 L + 20 L ethanol (94%) | Av = 150,000<br>n1 = 130,000<br>n2 = 170,000<br>Y&M not detected<br>n1, n2 not detected | No effect | No effect |

Conclusion:

The polyglycoside wetting agent (i.e. surfactant) was not bactericidal and can act as a food source for the bacteria Alcohol (50% concentration) applied at ratio of 40 L per 1 tonne peas was not a strong bactericidal agent on split pea.

Peracetic acid either preformed via liquid formulations or in-situ generated via powdered formulations, was a strong bactericidal agent and reduced the level of bacteria, yeast and mold significantly.

Wetting agent (i.e. surfactant) combined to peracetic acid formulations increased the efficiency of the oxidizer and showed to be synergistic with peracetic acid.

Alcohol (ethanol) combined to peracetic acid formulations increased the efficiency of the oxidizer and thus showed to be synergistic with peracetic acid.

Both alcohol and wetting agent (i.e. surfactant) increased the coverage of peracetic acid and helped this limited amount of solution (40 L per 1 tonne seed) to better cover the seeds and penetrate the seeds and target microorganisms.

They showed a synergistic effect that is higher than the one of the peracetic acid with a wetting agent or the peracetic acid with an alcohol.

TABLE 3

V- RESULTS on pea fiber

| Treatments | Total count Aerobic CFU/g bacteria | Physical Characteristics | Organoleptic |
|---|---|---|---|
| 0- Untreated | Av = 900,000<br>n1 = 700,000<br>n2 = 1.1 million<br>Av = 1,000 Y&M<br>n1 = 1000/n2 = 1000 | No effect | No effect |
| 1- Surfactant APG 325<br>0.5% | Av = 900,000<br>n1 = 850,000<br>n2 = 950,000<br>Av = 1,000 Y&M<br>n1 = 1000/n2 = 1000 | No effect | No effect |
| 2- Alcohol - ethanol<br>50% | Av = 700,000<br>n1 = 500,000<br>n2 = 900,000<br>Y&M not detected<br>n1, n2 not detected | No effect | No effect |
| 3- Powdered PAA Alone<br>4 kg/40 L | Av = 500,000<br>n1 = 700,000<br>n2 = 300,000<br>Y&M not detected<br>n1, n2 not detected | No effect | No effect |
| 4- Neo Pure<br>4 kg/40 L | Av = 500,000<br>n1 = 450,000<br>n2 = 550,000<br>Y&M not detected<br>n1, n2 not detected | No effect | No effect |
| 5- Neo Pure + alcohol<br>2 kg/20 L + 20 L ethanol (94%) | Av = 250,000<br>n1 = 200,000<br>n2 = 300,000<br>Y&M not detected<br>n1, n2 not detected | No effect | No effect |
| 6- Percid -Liquid PAA alone<br>8 L/40 L | Av = 600,000<br>n1 = 600,000<br>n2 = 600,000<br>Y&M not detected<br>n1, n2 not detected | No effect | No effect |
| 7- Percid -Liquid PAA<br>8 L/40 L + surfactant | Av = 400,000<br>n1 = 500,000<br>n2 = 300,000<br>Y&M not detected<br>n1, n2 not detected | No effect | No effect |
| 8- Percid -Liquid PAA + surfactant + alcohol (94%)<br>4 L/20 L + 20 L ethanol + surfactant | Av = 300,000<br>n1 = 330,000<br>n2 = 270,000<br>Y&M not detected<br>n1, n2 not detected | No effect | No effect |
| 9- Powdered PAA + alcohol (94%)<br>2 kg/20 L + 20 L ethanol | Av = 300,000<br>n1 = 400,000<br>n2 = 200,000<br>Y&M not detected<br>n1, n2 not detected | No effect | No effect |
| 10- Percid -Liquid PAA + alcohol 4 L/20 L +<br>20 L ethanol (94%) | Av = 450,000<br>n1 = 600,000<br>n2 = 300,000<br>Y&M not detected<br>n1, n2 not detected | No effect | No effect |

Conclusion:

The solution affected the fiber pea size due to humidity. However, drying can restore the size of fiber pea as the untreated.

The polyglycoside wetting agent (i.e. surfactant) was not bactericidal and can act as a food source for the bacteria Alcohol (50% concentration) applied at ratio of 40 L per 1 tonne peas was not a strong bactericidal agent on pea fiber at used concentration (i.e. 40 L of alcohol 50% active per 1 tonne).

Peracetic acid either preformed via liquid formulations or in-situ generated via powdered formulations, was a strong bactericidal agent and reduced the level of bacteria, yeast and mold significantly.

Wetting agent (i.e. surfactant) combined with peracetic acid formulation increased the efficiency of the oxidizer and thus showed to be synergistic with peracetic acid.

Alcohol (ethanol) combined with peracetic acid formulations increases the efficiency of the oxidizer and thus showed to be synergistic with peracetic acid.

Both alcohol and wetting agent (i.e. surfactant) increased the coverage of peracetic acid and helped this limited amount of solution (40 L per 1 tonne seed) to better cover the seeds and penetrate the seeds and target microorganisms. They showed a synergistic effect that is higher that the one of the peracetic acid with a wetting agent or the peracetic acid with an alcohol.

TABLE 4

VI- RESULTS on vanilla

| Treatments | Total count Aerobic CFU/g bacteria | Physical Characteristics | Organoleptic |
|---|---|---|---|
| 0- Untreated | Av = 2 millions<br>n1 = 1.5 millions<br>n2 = 2.5 millions<br>Av = 1,000 Y&M<br>n1 = 1000/n2 = 1000 | No effect | No effect |
| 1- Wetting agent APG 325 0.5% | Av = 2 millions<br>n1 = 1.3 millions<br>n2 = 2.7 millions<br>Av = 1,000 Y&M<br>n1 = 1000/n2 = 1000 | No effect | No effect |
| 2- Alcohol - ethanol 50% | Av = 1 million<br>n1 = 1 million<br>n2 = 1 million<br>Av = 1,000 Y&M<br>n1 = 1000/n2 = 1000 | No effect | No effect |
| 3- Powdered PAA Alone 4 kg/40 L | Av = 900,000<br>n1 = 600,000<br>n2 = 1.2 millions<br>Y&M not detected<br>n1, n2 not detected | No effect | No effect |
| 4- Neo Pure 4 kg/40 L | Av = 500,000<br>n1 = 600,000<br>n2 = 400,000<br>Y&M not detected<br>n1, n2 not detected | No effect | No effect |
| 5- Neo Pure + alcohol 2 kg/20 L + 20 L ethanol (94%) | Av = 200,000<br>n1 = 150,000<br>n2 = 250,000<br>Y&M not detected<br>n1, n2 not detected | No effect | No effect |
| 6- Percid -Liquid PAA alone 8 L/40 L | Av = 500,000<br>n1 = 600,000<br>n2 = 400,000<br>Y&M not detected<br>n1, n2 not detected | No effect | No effect |
| 7- Percid -Liquid PAA 8 L/40 L + wetting agent | Av = 300,000<br>n1 = 320,000<br>n2 = 280,000<br>Y&M not detected<br>n1, n2 not detected | No effect | No effect |
| 8- Percid -Liquid PAA + wetting agent + alcohol (94%) 4 L/20 L + 20 L ethanol + wetting agent | Av = 300,000<br>n1 = 310,000<br>n2 = 290,000<br>Y&M not detected<br>n1, n2 not detected | No effect | No effect |
| 9- Powdered PAA + alcohol (94%) 2 kg/20 L + 20 L ethanol | Av = 300,000<br>n1 = 300,000<br>n2 = 300,000<br>Y&M not detected<br>n1, n2 not detected | No effect | No effect |
| 10- Percid -Liquid PAA + alcohol 4 L/20 L + 20 L ethanol (94%) | Av = 300,000<br>n1 = 330,000<br>n2 = 270,000<br>Y&M not detected<br>n1, n2 not detected | No effect | No effect |

Conclusion:

The solutions were sprayed on vanilla as received in rod shape to reduce the level of total aerobic count.

The polyglycoside wetting agent (i.e. surfactant) was not bactericidal and can act as a food source for the bacteria Alcohol (50% concentration) applied at ratio of 40 L per 1 tonne vanilla was not a strong bactericidal agent on vanilla.

Peracetic acid either preformed via liquid formulations or generated in-situ via powdered formulations, was a strong bactericidal agent and reduced the level of bacteria, yeast and mold significantly.

Wetting agent (i.e. surfactant) combined with peracetic acid formulations increased the efficiency of the oxidizer and thus showed to be synergistic with peracetic acid.

Alcohol (ethanol) combined with peracetic acid formulations increased the efficiency of the oxidizer and thus showed to be synergistic with peracetic acid.

Both alcohol and wetting agent (i.e. surfactant) increased the coverage of peracetic acid and helped this limited amount of solution (40 L per 1 tonne seed) to better cover the seeds and penetrate the seeds and target microorganisms. They showed a synergistic effect that is higher than the one of the peracetic acid with a wetting agent or the peracetic acid with an alcohol.

TABLE 5

VII- RESULTS on chia seeds

| Treatments | Total count Aerobic CFU/g bacteria | Physical Characteristics | Organoleptic |
|---|---|---|---|
| 0- Untreated | Av = 1 million<br>n1 = 1.1 million<br>n2 = 900,000<br>Av = 10,000 Y&M<br>n1 = 10,000/n2 = 10,000 | Mucilage observed | No effect |
| 1- Wetting agent APG 325 0.5% | Not tested due to mucilage | Mucilage observed | Mucilage observed |
| 2- Alcohol - ethanol 50% | Av = 510,000<br>n1 = 520,000<br>n2 = 500,000<br>Av = 10,000 Y&M<br>n1 = 10,000/n2 = 10,000 | No mucilage | No mucilage |
| 3- Powdered PAA Alone 4 kg/40 L | Not tested due to mucilage | Mucilage observed | Mucilage observed |
| 4- Neo Pure 4 kg/40 L | Not tested due to mucilage | Mucilage observed | Mucilage observed |
| 5- Neo Pure + alcohol 2 kg/20 L + 20 L ethanol (94%) | Av = 300,000<br>n1 = 330,000<br>n2 = 270,000<br>Av = 1,000 Y&M<br>n1 = 1,000/n2 = 1,000 | No mucilage | No effect. |
| 6- Percid -Liquid PAA alone 8 L/40 L | Not tested due to mucilage | Mucilage observed | Mucilage observed |
| 7- Percid -Liquid PAA 8 L/40 L + wetting agent | Not tested due to mucilage | Mucilage observed | Mucilage observed |
| 8- Percid -Liquid PAA + wetting agent + alcohol (94%) 4 L/20 L + 20 L ethanol + surfactant | Av = 300,000<br>n1 = 350,000<br>n2 = 250,000<br>Av = 1,000 Y&M<br>n1 = 1,000/n2 = 1,000 | No mucilage | No effect. |
| 9- Powdered PAA + alcohol (94%) 2 kg/20 L + 20 L ethanol | Av = 400,000<br>n1 = 420,000<br>n2 = 380,000<br>Av = 1,000 Y&M<br>n1 = 1,000/n2 = 1,000 | No mucilage | No effect. |
| 10- Percid -Liquid PAA + alcohol 4 L/20 L + 20 L ethanol (94%) | Av = 200,000<br>n1 = 150,000<br>n2 = 250,000<br>Y&M not detected<br>n1, n2 not detected | No mucilage | No effect. |

Conclusion:
The presence of alcohol prevents the release of mucilage.
The PAA in 50% Alcohol seems efficacious in reducing bacteria and yeast.

TABLE 6

| | VIII- RESULTS on flax seeds | | |
|---|---|---|---|
| Treatments | Total count Aerobic CFU/g bacteria | Physical Characteristics | Organoleptic |
| 0- Untreated | Av = 5 millions<br>n1 = 6.5 millions<br>n2 = 3.5 millions<br>Av = 1,000 Y&M<br>n1 = 1,000/n2 = 1,000 | Mucilage observed | No effect |
| 1- Wetting agent APG 325 0.5% | Not tested due to mucilage | Mucilage observed | Mucilage observed |
| 2- Alcohol - ethanol 50% | Av = 2 millions<br>n1 = 1.8 millions<br>n2 = 2.2 millions<br>Av = 1,000 Y&M<br>n1 = 1,000/n2 = 1,000 | No mucilage | No mucilage |
| 3- Powdered PAA Alone 4 kg/40 L | Not tested due to mucilage | Mucilage observed | Mucilage observed |
| 4- Neo Pure 4 kg/40 L | Not tested due to mucilage | Mucilage observed | Mucilage observed |
| 5- Neo Pure + alcohol 2 kg/20 L + 20 L ethanol (94%) | Av = 1 million<br>n1 = 1 million<br>n2 = 1 million<br>Y&M not detected<br>n1, n2 not detected | No mucilage | No effect. |
| 6- Percid -Liquid PAA alone 8 L/40 L | Not tested due to mucilage | Mucilage observed | Mucilage observed |
| 7- Percid -Liquid PAA 8 L/40 L + wetting agentt | Not tested due to mucilage | Mucilage observed | Mucilage observed |
| 8- Percid -Liquid PAA + wetting agent + alcohol (94%) 4 L/20 L + 20 L ethanol + surfactant | Av = 700,000<br>n1 = 850,000<br>n2 = 550,000<br>Y&M not detected<br>n1, n2 not detected | No mucilage | No effect. |
| 9- Powdered PAA + alcohol (94%) 2 kg/20 L + 20 L ethanol | Av = 900,000<br>n1 = 915,000<br>n2 = 885,000<br>Y&M not detected<br>n1, n2 not detected | No mucilage | No effect. |
| 10- Percid -Liquid PAA + alcohol 4 L/20 L + 20 L ethanol (94%) | Av = 800,000<br>n1 = 800,000<br>n2 = 800,000<br>Y&M not detected<br>n1, n2 not detected | No mucilage | No effect. |

Conclusion:
The presence of alcohol prevented the release of mucilage.
Macroscopically, mucilage was not observed on seeds treated with alcohol.
The PAA in 50% alcohol was efficacious in reducing bacteria and yeast.

TABLE 7

| | IX- RESULTS on sprouted flax and chia | | |
|---|---|---|---|
| Treatments | Total count Aerobic CFU/g bacteria | Physical Characteristics | Organoleptic |
| 0- Untreated | Av = 2 millions<br>n1 = 2.5 millions<br>n2 = 1.5 millions<br>Av = 1,000 Y&M<br>n1 = 1,000/n2 = 1,000 | Mucilage observed, very wet | No effect |
| 1- Wetting agent APG 325 0.5% | Not tested due to mucilage | Mucilage observed | Mucilage observed |

TABLE 7-continued

| | IX- RESULTS on sprouted flax and chia | | |
|---|---|---|---|
| Treatments | Total count Aerobic CFU/g bacteria | Physical Characteristics | Organoleptic |
| 2- Alcohol - ethanol 50% | Av = 600,000 n1 = 550,000 n2 = 650,000 Av = 1,000 Y&M n1 = 1,000/n2 = 1,000 | No mucilage | No mucilage |
| 3- Powdered PAA Alone 4 kg/40 L | Not tested due to mucilage | Mucilage observed | Mucilage observed |
| 4- Neo Pure 4 kg/40 L | Not tested due to mucilage | Mucilage observed | Mucilage observed |
| 5- Neo Pure + alcohol 2 kg/20 L + 20 L ethanol (94%) | Av = 200,000 n1 = 220,000 n2 = 180,000 Y&M not detected n1, n2 not detected | No mucilage | No effect. |
| 6- Percid -Liquid PAA alone 8 L/40 L | Not tested due to mucilage | Mucilage observed | Mucilage observed |
| 7- Percid -Liquid PAA 8 L/40 L + wetting agent | Not tested due to mucilage | Mucilage observed | Mucilage observed |
| 8- Percid -Liquid PAA + wetting agent + alcohol (94%) 4 L/20 L + 20 L ethanol + wetting agent | Av = 500,000 n1 = 525,000 n2 = 475,000 Y&M not detected n1, n2 not detected | No mucilage | No effect. |
| 9- Powdered PAA + alcohol (94%) 2 kg/20 L + 20 L ethanol | Av = 600,000 n1 = 600,000 n2 = 600,000 Y&M not detected n1, n2 not detected | No mucilage | No effect. |
| 10- Percid -Liquid PAA + alcohol 4 L/20 L + 20 L ethanol (94%) | Av = 600,000 n1 = 500,000 n2 = 700,000 Y&M not detected n1, n2 not detected | No mucilage | No effect. |

Conclusion:

Humidity including alcohol solution may affect the sprouted flax and chia. It should be dried well.

The presence of alcohol was shown to prevent the release of mucilage

Alcohol was shown to act as a bactericidal agent but not very strong.

The PAA in 50% alcohol was shown to be efficacious in reducing bacteria and yeast.

Macroscopically, mucilage was not observed on seeds treated with alcohol.

TABLE 8

| | X- RESULTS on hemp | | |
|---|---|---|---|
| Treatments | Total count Aerobic CFU/g bacteria | Physical Characteristics | Organoleptic |
| 0- Untreated | Av = 2 millions n1 = 1.7 millions n2 = 2.3 millions Av = 1,000 Y&M n1 = 1000/n2 = 1000 | No effect | No effect |
| 1- Wetting agent APG 325 0.5% | Av = 2 millions n1 = 1.5 millions n2 = 2.5 millions Av = 1,000 Y&M n1 = 1000/n2 = 1000 | No effect | No effect |
| 2- Alcohol - ethanol 50% | Av = 1 million n1 = 800,000 n2 = 1.2 millions Av = 1,000 Y&M n1 = 1000/n2 = 1000 | No effect | No effect |
| 3- Powdered PAA Alone 4 kg/40 L | Av = 500,000 n1 = 600,000 n2 = 400,000 Y&M not detected n1, n2 not detected | No effect | No effect |

TABLE 8-continued

X- RESULTS on hemp

| Treatments | Total count Aerobic CFU/g bacteria | Physical Characteristics | Organoleptic |
|---|---|---|---|
| 4- Neo Pure 4 kg/40 L | Av = 300,000<br>n1 = 300,000<br>n2 = 300,000<br>Y&M not detected<br>n1, n2 not detected | No effect | No effect |
| 5- Neo Pure + alcohol 2 kg/20 L + 20 L ethanol (94%) | Av = 100,000<br>n1 = 120,000<br>n2 = 80,000<br>Y&M not detected<br>n1, n2 not detected | No effect | No effect |
| 6- Percid -Liquid PAA alone 8 L/40 L | Av = 310,000<br>n1 = 300,000<br>n2 = 320,000<br>Y&M not detected<br>n1, n2 not detected | No effect | No effect |
| 7- Percid -Liquid PAA 8 L/40 L + wetting agent | Av = 300,000<br>n1 = 320,000<br>n2 = 280,000<br>Y&M not detected<br>n1, n2 not detected | No effect | No effect |
| 8- Percid -Liquid PAA + wetting agent + alcohol (94%) 4 L/20 L + 20 L ethanol + surfactant | Av = 200,000<br>n1 = 100,000<br>n2 = 300,000<br>Y&M not detected<br>n1, n2 not detected | No effect | No effect |
| 9- Powdered PAA + alcohol (94%) 2 kg/20 L + 20 L ethanol | Av = 200,000<br>n1 = 200,000<br>n2 = 200,000<br>Y&M not detected<br>n1, n2 not detected | No effect | No effect |
| 10- Percid -Liquid PAA + alcohol 4 L/20 L + 20 L ethanol (94%) | Av = 300,000<br>n1 = 330,000<br>n2 = 270,000<br>Y&M not detected<br>n1, n2 not detected | No effect | No effect |

Conclusion:

The above-mentioned solutions were sprayed on hemp seeds to achieve a reduction of the level of total aerobic count.

The polyglycoside wetting agent (i.e. surfactant) was not bactericidal.

Alcohol (50% concentration) applied at ratio of 40 L per 1 tonne hemp seed was not a strong bactericidal agent on hemp.

Peracetic acid either preformed via liquid formulations or generated in-situ via powdered formulations, was a strong bactericidal agent and reduced the level of bacteria, yeast and mold significantly.

Wetting agent (i.e. surfactant) combined with peracetic acid formulations increased the efficiency of the oxidizer and thus showed to be synergistic with peracetic acid.

Alcohol (ethanol) combined with peracetic acid formulations increased the efficiency of the oxidizer and thus showed to be synergistic with peracetic acid.

Both alcohol and surfactant increase the coverage of peracetic acid and help this limited amount of solution (40 L per 1 tonne seed) to better cover the seeds and penetrate the seeds and target microorganisms. They showed a synergistic effect that is higher than that of the peracetic acid with a wetting agent or the peracetic acid with an alcohol.

TABLE 9

XI- Results on black pepper

| Treatments | Total count Aerobic CFU/g bacteria | Physical Characteristics | Organoleptic |
|---|---|---|---|
| 0- Untreated | Av = 1.5 millions<br>Av = 3,000 Y&M | No effect | No effect |
| 1- Surfactant APG 325 0.5% | Av = 1.7 millions<br>Av = 3,000 Y&M | No effect | No effect |
| 2- Alcohol - ethanol 50% | Av = 1 million<br>Av = 1,000 Y&M | No effect | No effect |
| 3- Powdered PAA Alone 4 kg/40 L | Av = 500,000<br>Av = 100 Y&M | No effect | No effect |
| 4- Neo Pure 4 kg/40 L | Av = 480,000<br>Av = 100 Y&M | No effect | No effect |

TABLE 9-continued

XI- Results on black pepper

| Treatments | Total count Aerobic CFU/g bacteria | Physical Characteristics | Organoleptic |
|---|---|---|---|
| 5- Neo Pure + alcohol 2 kg/20 L + 20 L ethanol (94%) | Av = 370,000 Av = 100 Y&M | No effect | No effect |
| 6- Percid -Liquid PAA alone 8 L/40 L | Av = 460,000 Y&M not detected | No effect | No effect |
| 7- Percid -Liquid PAA 8 L/40 L + surfactant | Av = 400,000 Y&M not detected | No effect | No effect |
| 8- Percid -Liquid PAA + surfactant + alcohol (94%) 4 L/20 L + 20 L ethanol + surfactant | Av = 380,000 Y&M not detected | No effect | No effect |
| 9- Powdered PAA + alcohol (94%) 2 kg/20 L + 20 L ethanol | Av = 400,000 Y&M not detected | No effect | No effect |
| 10- Percid -Liquid PAA + alcohol 4 L/20 L + 20 L ethanol (94%) | Av = 380,000 Y&M not detected | No effect | No effect |

Conclusion:

The disinfecting solutions sprayed on black pepper seeds can reduce the level of total aerobic count.

The polyglycoside surfactant is not bactericidal.

Alcohol (50% concentration) applied at ratio of 40 L per 1 tonne black pepper seed is not a strong bactericidal agent on hemp.

Peracetic acid either preformed via liquid formulations or generated in-situ via powdered formulations, is a strong bactericidal agent and reduces the level of bacteria, yeast and mold significantly.

Alcohol (ethanol) combined with peracetic acid formulations increases the efficiency of the oxidizer and thus is synergistic with peracetic acid.

Both alcohol and surfactant increase the coverage of peracetic acid and help this limited amount of solution (40 L per 1 tonne seed) to better cover the seeds and penetrate the seeds and target microorganisms.

Example 2

A Trial Assessing the Efficacy of Powdered Formula (Powdered PAA with a Wetting Agent) in the Surface Disinfection of Hemp Seeds in a Grain Conditioning Facility Protocol:

Several tonnes of hemp seeds were cleaned mechanically using regular grain conditioning equipment. The total bacterial count was determined to be about 18 million CFU/g (before mechanical cleaning and separation). After mechanical cleaning, the total bacterial count was found to be about 2 million CFU/g. This microbial load does not comply with the market standard which is 1 million CFU/g.

Treatment with Peracetic Acid and Hydrogen Peroxide without an Alcohol and/or a Wetting Agent:

Hemp seeds (with a microbial load of about 2 million CFU/g) were sanitized with a powdered product based on sodium percarbonate, TAED and citric acid that generates peracetic acid and hydrogen peroxide in situ. An equivalent of 4 kg of this formula were dissolved in potable water and mixed thoroughly for 10 minutes and then applied to 1 tonne of hemp seeds and allowed to remain in contact with them for 30 minutes. The seeds were thoroughly dried after the treatment. The results did not show a significant reduction in microbial load as compared to untreated seeds (2 million CFU/g). These results were not satisfactory. In addition, coliforms, E. coli, yeast and mold were detected. The powdered formulation that generates PAA in-situ was based on 70% w/w sodium percarbonate, mixed with 20% w/w TAED and mixed with 10% citric acid.

Treatment with Formula (Peracetic Acid Generated In-Situ with a Wetting Agent):

1 tonne of cleaned hemp seeds (2 million CFU per gram) were sanitized with a 0.4% concentration (4 kg of formula 18/18). Said formula 18/18 is powdered formulation is based on 40% sodium percarbonate, mixed with 20% TAED; mixed with 18% potassium silicate; mixed with 18% EDTA acid; and finally mixed with 4% Bioterge AS 90 surfactant. The 4 kg were diluted in 40 L water and were mixed thoroughly for 10 minutes and then applied to treat 1 tonne of hemp seed for 30 minutes, then the treated seeds were dried very well as per the grain conditioner process. The results showed a reduction in total bacterial count to 54,000 CFU per gram. These results were satisfactory and complied with the market standards. Coliforms, E. coli, yeast and mold were not detected.

Conclusions:

Based on the results shown above, there was noted a synergy between oxidizers (i.e. peracetic acid and hydrogen peroxide) and wetting agent (i.e. surfactant) in reducing the populations of human pathogens on edible seeds.

Example 3

Determination of Contact-Time Efficacy of Powdered PAA Combined with Alcohol and a Wetting Agent Objective:

The objective of this study is to determine the effective contact-time of the sanitizing solutions (PAA with an alcohol and a wetting agent) sprayed on hemp seeds in controlling pathogens.

Protocol:

1 kg of hemp seeds per mix was treated with 50 ml of solution by applying small amounts at a time using a hand sprayer and mixing thoroughly in between. Batches were stored in 3.3 L containers at room temperature with lids on to avoid loss of moisture due to evaporation.

Solutions Used:

Neo-Pure (5%), (50 g Neo Pure dissolved in 1 L water and mixed for 15 minutes)

Neo-Pure/Ethanol (5% Neo Pure dissolved in 50% water/50% alcohol),

Mock ($H_2O$)

Samples were taken at the indicated time points and plated immediately with the exception of the +1 hr time point in the experiment of 8/25 (This sample was taken at +1 hr but stored at 4° C. o/n and plated the next morning).

Results

Batch Treatment 2014-08-25

Triplicates

TABLE 10

|  | +1 hr | +21 hrs | +48 hrs | +72 hrs |
|---|---|---|---|---|
| UTC | 786,000 | 3,200,000 | 620,000 | 890,000 |
| mock | 701,000 | 793,000 | 400,000 | 765,000 |
| Neo-Pure | 1,000,000 | 195,000 | 272,000 | 101,000 |
| Neo-Pure EtOH | 182,000 | 23,000 | 22,000 | 73,000 |

Figure 2:
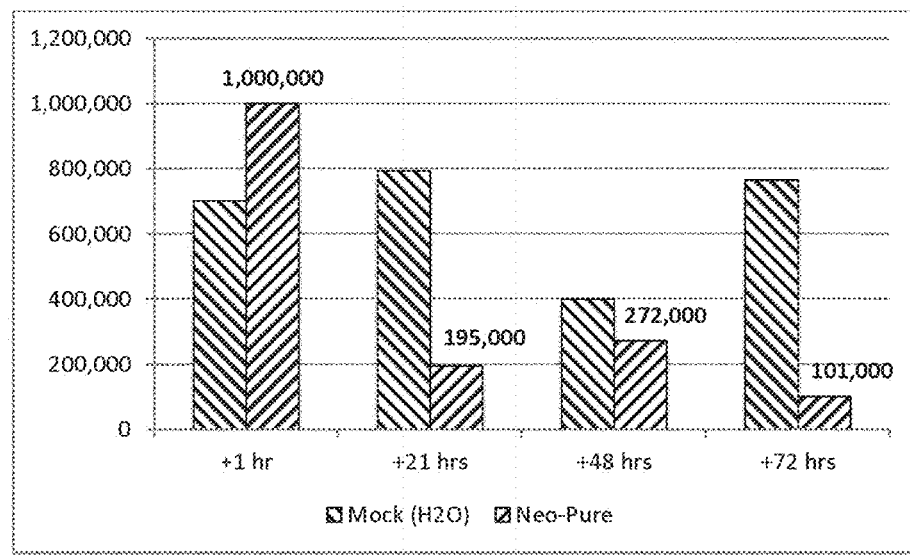
Figure 3:
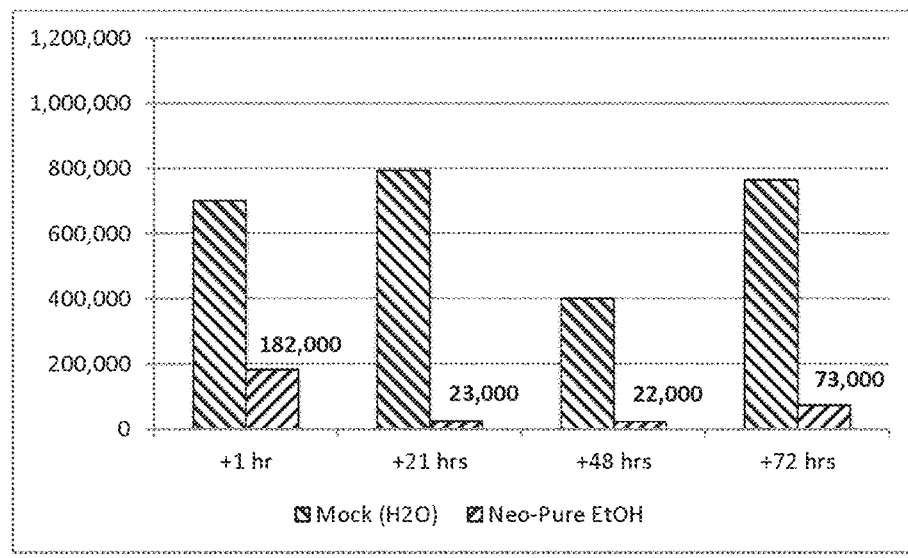

UTC means untreated and aforesaid data were reported on FIGS. 1 to 3.

Batch Treatment 2014-09-10

Pentuplicates

TABLE 11

|  | starting point | +3 hr | o/n | +24 hrs | +48 hrs |
|---|---|---|---|---|---|
| UTC | 12,700,000 |  |  |  |  |
| Neo-Pure |  | 17,700,000 | 8,400,000 | 2,660,000 | 4,520,000 |
| Neo-Pure EtOH |  | 2,400,000 | 1,600,000 | 1,600,000 | 1,480,000 |

Figure 4:
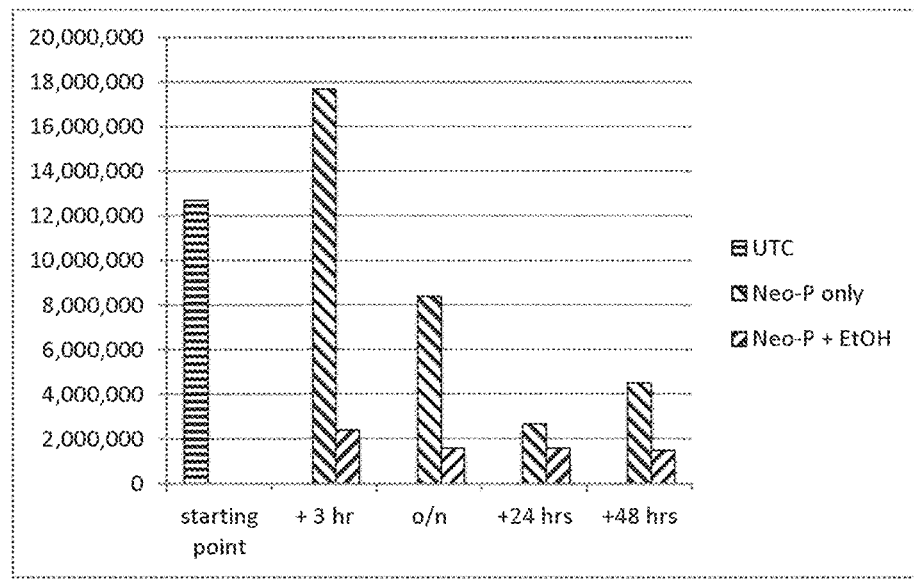
FIGS. 4 to 6 represent results obtained according to Example 3.
Figure 5:
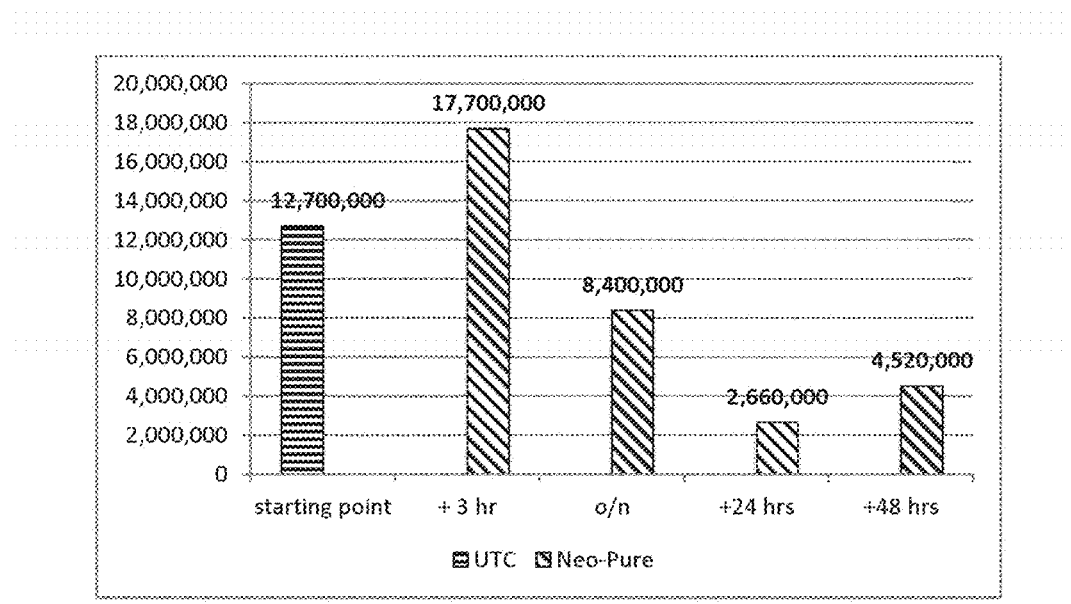
Figure 6:
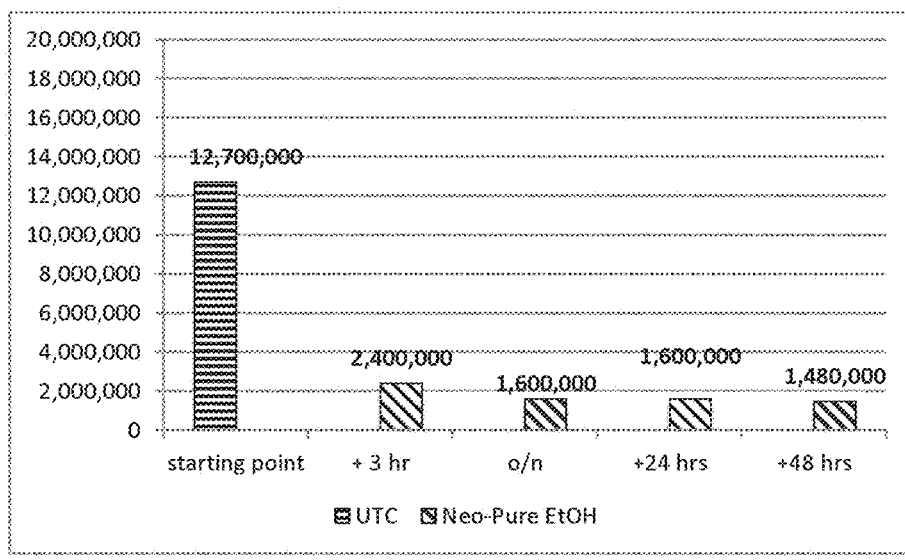

UTC means untreated and aforesaid data were reported on FIGS. 4 to 6.

Conclusions:

Under lab conditions (room temperature: 20° C. to 27° C.) the efficacy of both Neo-Pure only and Neo-Pure+EtOH increased significantly with longer incubation times (24 hours)

This effect was much more prominent at the beginning of the treatment with Neo-Pure only. However, it was noted that no significant regrowth of bacteria was observed within the first 48 hours post treatment if EtOH was present.

Once seeds were treated with PAA+alcohol and/or wetting agent, the sanitizing solution continues to work for hours and reduce the population of bacteria. However, after 48 hrs, seeds had to be dried to reduce the moisture content below 10% in order to prevent regrowth of microorganisms. A moisture content below 10% is a usual standard of the industry to prevent a growth of microorganisms.

Chia Seed Treatment in Small Batches with 50% Ethanol 1 kg aliquots of chia seeds were weighted into clean containers sterilized with 70% ethanol. Neo-Pure solution was prepared by dissolving Neo-Pure powder (a powdered peracetic acid precursor available from Agri-Neo) in tap water to a final concentration of 10% (w/v) and incubated at room temperature (RT) for 15 minutes to allow the formation of active peracetic acid (PAA) as the active ingredient. Subsequently, ethanol was added to a final concentration of 50% (v/v) to generate sanitizing solution containing 5% Neo-Pure (w/v) and 50% ethanol (v/v). 50 ml solution (target rate: 50 l/tonne) was applied to the seeds under vigorous mixing using a small hand vaporizer; PAA activity was confirmed to be >160 ppm using test strips (LaMotte Insta-Test Analytic Peracetic Acid) during application. Post treatment, all aliquots were stored at RT in sealed containers until sampling. Samples were taken 12 and 24 hours post treatment and plated on 3M Petrislides within 2 hours of sampling to determine total aerobic counts.

Sample processing was conducted according to manufacturers recommendations; in brief, 7 g sample were added to 700 ml water and homogenized for 2 min using a handmixer. A dilution series was generated using sterile 9 ml buffered peptone water aliquots (3M) and 1 ml of the relevant dilutions were plated onto 3M Petrifilm Aerobic Count Plates. Petrifilms were incubated at 31° C. for 72 hours before counting.

The results of these trials are summarized in the table below.

TABLE 12

|  | Untreated | Treated 50 l/tonne | | Treated 100 l/tonne | |
|---|---|---|---|---|---|
|  |  | Incubated 12 hrs | Incubated 24 hrs | Incubated 12 hrs | Incubated 24 hrs |
| Total Aerobic Count (CFU/g) | $4 \times 10^6$ | $1.6 \times 10^6$ | $3.8 \times 10^5$ | $8.8 \times 10^5$ | $3.2 \times 10^5$ |
| Coliforms (CFU/g) | $1.5 \times 10^4$ | $1.4 \times 10^3$ | 600 | $1.4 \times 10^3$ | 400 |

As indicated in the table above, at 5% Neo-Pure, 50% ethanol, chia seeds were successfully sanitized. Extending contact time up to 24 hrs improved efficacy. There was no significant benefit demonstrated to applying the treatment solution at a rate higher than 50 l/tonne. Mucilage release was completely suppressed.

Treatment of Mucilaginous Seeds with Alcohol at 20% and Lower Concentrations

Tests were conducted to determine (a) whether a 20% ethanol formulation, which is combustible but not flammable, would effectively sanitize seeds and (b) the minimum ethanol concentration required to prevent mucilage release.

A treatment solution was generated composed of (a) water: balance up to 100% (v/v), (b) Neo-Pure: 10% (v/v), and (c) Active Ethanol: 20% (v/v). A minimum of 4 ml of the treatment solution was sprayed, using a handheld atomizing sprayer while mixing, on 100 gram samples of chia and flax seeds. The samples were allowed to air dry and checked for mucilage. No mucilage was observed for either the flax or chia seeds. This same experiment was repeated with 19%, 18%, 17% and 16% ethanol in the treatment solution with no mucilage observed. The experiment was repeated again with 15% ethanol in the treatment solution and about around 5% of the seeds (both flax and chia) released mucilage. The experiment was repeated again with 14% ethanol in the treatment solution and significant amounts of mucilage production were observed.

Another treatment solution was made up composed of (a) water: balance up to 100% (v/v), (b) Neo-Pure: 10% (v/v), (c) Active Ethanol: 10% (v/v) and (d) Propylene Glycol 10% (v/v). A minimum of 4 ml of the treatment solution was sprayed, using a handheld atomizing sprayer while mixing, on 100-gram samples of chia and flax seeds. The samples were allowed to air dry and checked for mucilage. No mucilage was observed for either the flax or chia seeds. This same experiment was repeated with 10% ethanol and 5% propylene glycol with no mucilage observed. However, in further experiments with 10% ethanol and less than 5% propylene glycol, some mucilage was observed.

Treatment of Various Seeds with 20% Solvent Treatment Solutions 150 g aliquots of various types of seeds were weighted into clean containers sterilized with 70% ethanol to generate treated and untreated control samples. 10 ml liquid Neo-Pure was mixed with 70 ml water and 20 ml ethanol added to obtain 100 ml of a treatment mixture containing 10% Neo-Pure (0.5% peracetic acid (PAA) w/v final concentration active ingredient) and 20% v/v ethanol. 7.5 ml solution (target rate: 50 l/tonne) were applied to the seeds under vigorous mixing using a small hand vaporizer; PAA activity was confirmed to be >160 ppm using test strips (LaMotte Insta-Test Analytic Peracetic Acid) during application. Post spraying, the final application rate was confirmed by determining weight added to the sample.

Seeds were stored at room temperature over night. After approximately 16 hours, 3 independent 10 g aliquots were removed from treated and untreated seed pools and processed to be analyzed on 3M Petrifilm slides to determine total aerobic counts. Sample processing was conducted according to manufacturers recommendations; in brief, 10 g sample and 90 ml sterile buffered peptone water (3M) were transferred into a sterile FBAG-04 filter blender bag and processed in a stomacher at 300 rpm for 1 min. A dilution series was generated using sterile 9 ml buffered peptone water aliquots (3M) and 1 ml of the relevant dilutions were plated onto 3M Petrifilm Aerobic Count Plates. Petrifilms were incubated at 31° C. for 72 hours before counting.

Results for sprouted flax seed are summarized in the table below.

TABLE 13

| Sample | Total Aerobic Count (CFU/g) | Standard Deviation | P-Value |
|---|---|---|---|
| Sprouted flax, untreated control | $268 \times 10^6$ | $6 \times 10^6$ | 0.0000003 |
| Sprouted flax, treated at 50 l/tonne | $15 \times 10^6$ | $2 \times 10^6$ | |

Results for sprouted white *quinoa* seeds are summarized in the table below.

TABLE 14

| Sample | Total Aerobic Count (CFU/g) | Standard Deviation | P-Value |
|---|---|---|---|
| Sprouted white quinoa, untreated control | $265 \times 10^6$ | $20 \times 10^6$ | 0.0000239 |
| Sprouted white quinoa, treated at 56 l/tonne | $5 \times 10^6$ | $2 \times 10^6$ | |

Results for sprouted white millet seeds are summarized in the table below.

TABLE 15

| Sample | Total Aerobic Count (CFU/g) | Standard Deviation | P-Value |
|---|---|---|---|
| Sprouted millet, untreated control | $7 \times 10^5$ | $8 \times 10^5$ | 0.194 |
| Sprouted millet, treated at 53 l/tonne | $3 \times 10^3$ | $5 \times 10^3$ | |

Results for sprouted amaranth seeds are summarized in the table below.

TABLE 16

| Sample | Total Aerobic Count (CFU/g) | Standard Deviation | P-Value |
|---|---|---|---|
| Sprouted amaranth, untreated control | $4.8 \times 10^6$ | $9.6 \times 10^4$ | 0.001 |
| Sprouted amaranth, treated at 53 l/tonne | $<1 \times 10^4$ | 0 | |

Results for a blend of sprouted seeds including flax and chia are summarized in the table below.

TABLE 17

| Sample | Total Aerobic Count (CFU/g) | Standard Deviation | P-Value |
|---|---|---|---|
| Sprouted seed blend, untreated control | $14 \times 10^6$ | $2.8 \times 10^6$ | 0.000004 |
| Sprouted seed blend, treated at 44 l/tonne | $3 \times 10^5$ | $1 \times 10^5$ | |

Treatment of the seeds described above with a Neo-Pure solution containing 20% ethanol reduced total aerobic counts on these seeds by 95%-99.5% with no negative effect on seed appearance and no detectable release of mucilage.

Initial Application Method

Figure 7:
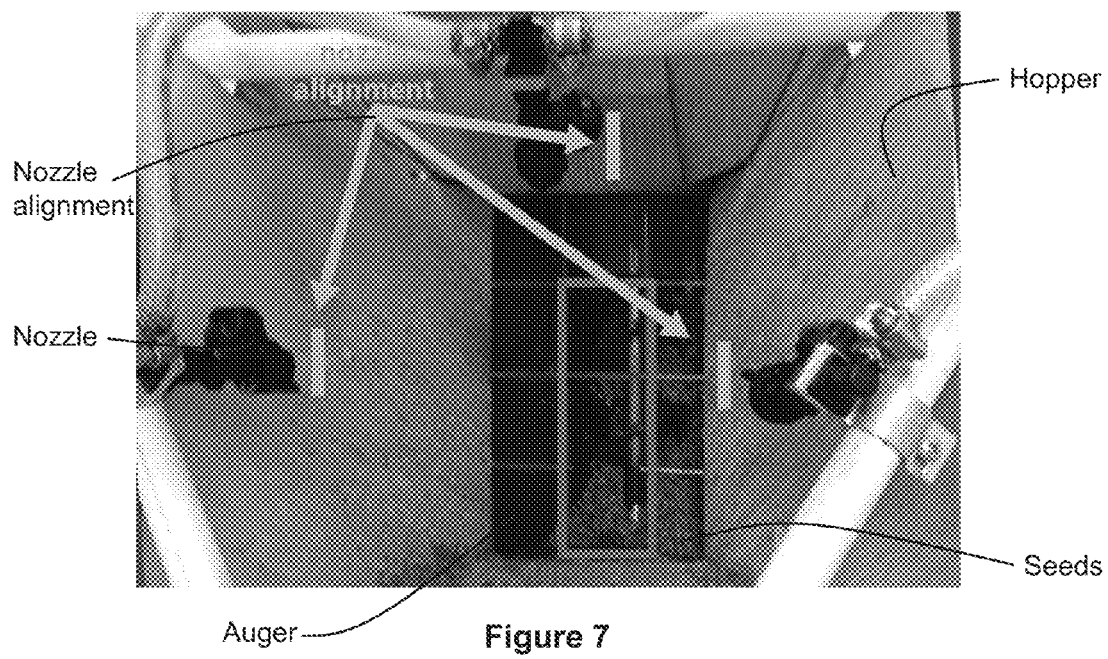
FIG. 7 is a photograph of an application device having a sprayer, a hopper and an auger.

Large scale production runs were simulated in a lab using a small hopper and auger setup to treat larger amount of seeds in a semi-continuous system. Hemp or Chia seeds were released from a reservoir and fell into a hopper. The hopper drained into an auger at the bottom of the hopper. A treatment solution containing 5% Neo-Pure powder (w/v) and 50% ethanol (v/v) was applied to the seeds as they fell into the hopper by a nozzle array consisting of three 8001vs nozzles operating at 30 psi (see FIG. 7). Further mixing of the treatment solution and the seeds occurred as the seeds traveled through the auger.

The nozzles were adjusted to generate a target delivery rate but treatment solution volumes before and after the runs (leftover) were measured to determine actual application rates. The runs described below were not performed in parallel but at different dates.

Samples were either taken immediately (hemp) or 24 hours (chia) after treatment and plated on 3M Petrislides within 2 hours of sampling to determine total aerobic microorganism counts. Sample processing was conducted according to manufacturers recommendations. In brief, a 7 g sample was added to 700 ml water and homogenized for 2 min using a handmixer. A dilution series was generated using sterile 9 ml buffered peptone water aliquots (3M) and 1 ml of the relevant dilutions were plated onto 3M Petrifilm Aerobic Count Plates. Petrifilms were incubated at 31° C. for 72 hours before counting.

For the hemp seed samples, processed and plated immediately after treatment, the lack of a post-treatment incubation period is expected to have lowered the apparent efficacy of the treatment based on other results presented further above. Two trials with hemp seeds were conducted using identical settings but for different treatment solution application rates. 57 l/tonne was applied in the first trial and 113 l/tonne was applied in the second run. The total aerobic counts measured are presented in the table below.

TABLE 18

| Seed Type | ACC untreated, (CFU/g) | ACC treated 57 l/tonne (CFU/g) | ACC treated 113 l/tonne (CFU/g) |
|---|---|---|---|
| Hemp | $7.5 \times 10^6$ | $4.6 \times 10^5$ | $2.9 \times 10^5$ |

As indicated in the table above, aerobic count was reduced 94% in the first trial and 96% in the second trial. This efficacy would likely have been higher if an incubation period (for example 24 hours) had been applied.

For the chia seed trial, the seeds were incubated over night after treatment. The treatment solution application rate was 120 l/tonne. Aerobic count results are presented in the table below.

TABLE 19

| Seed Type | ACC untreated, (CFU/g) | ACC treated 120 l/tonne, incubated (CFU/g) | p-value |
|---|---|---|---|
| Chia | $4.5 \times 10^5$ | $1.4 \times 10^6$ | 0.12 |

No significant reduction in microbial load was observed after treatment of the chia seeds even though the application rate was higher than for the hemp seeds. Numerically, ACC counts were higher after treatment and incubation than in the untreated sample, but the numerical difference was not statistically significant.

Both seed types can be efficiently sanitized with Neo-Pure in small scale batch experiments and so the chemistry of the treatment solution is not believed to be the underlying cause of this difference. The most prominent difference between hemp and chia seeds is their capacity to produce mucilage, chia being the more mucilaginous seed. Without intending to be limited by theory, the inventors believe that the combination of a mucilaginous seed with a sprayed application of the treatment solution is responsible for the lack of activity in the chia trial described above. Mucilage in the seed coat may be able to inactivate, absorb or consume peractic acid. In the small scale batch experiments, the treatment solution was applied to the seeds through an atomizing sprayer. The atomizing sprayer increases the initial contact surface, or the initial dispersion of treatment solution across the seed, relative to the nozzles used over the hopper, which delivered a generally continuous stream of treatment solution. The improved initial dispersion of the treatment solution with an atomizing sprayer may allow the treatment solution to neutralize more microbes before it becomes deactivated. With the sprayer, hopper and auger set-up, the initial seed contact surface is more limited and more nearly complete dispersion of the treatment solution may not occur until the seeds are mixed in the auger. Although secondary distribution occurs in the auger within seconds of the initial application, in the case of mucilaginous seeds a significant part of the treatment solution activity may be compromised by mucilage if the treatment solution is not well dispersed around the seed on initial contact. Hemp, in contrast, does not produce mucilage, and is adequately treated even if the initial application of the treatment solution is more concentrated. Consequently, secondary distribution of treatment solution is believed to be sufficient for the treatment of non-mucilaginous seeds.

To investigate the issues described above, and to develop a large scale treatment process suitable for mucilaginous seeds, further trials with chia seeds were performed using a commercial seed treater (USC Continuous Treating System, USC LLC, KS). Seed treaters are typically used to apply small volumes of antimicrobial or antifungal agents to seeds before they are planted. In the seed treater tested, seeds fall from a hopper onto a seed wheel. The seed wheel scatters the seeds, and the seeds then fall through an atomizing chamber. In the atomizing chamber, an atomizing sprayer spins while producing a mist of the applied agent. The overall effect is that the seeds are separated from each other and fall through a mist of the applied agent which provides a well dispersed initial application of the agent. The seeds fall into a horizontal drum with paddles installed along the length of the drum in a staggered pattern, which provides some secondary mixing.

In an exemplary trial, the seed treater was used to apply a treatment solution as discussed above to 750 ponds of chia seeds at an application rate of 50 l/tonne. The treated seeds were incubated overnight and samples were plated the next day. Count results are presented in the table below.

TABLE 20

| | | Aerobic count (CFU/g) | Yeast count (CFU/g) | Mold count (CFU/g) | Conforms count (CFU/g) |
|---|---|---|---|---|---|
| Chia | Untreated | None detected | 704 | 190 | 35 |
| | Treated | None detected | None detected | None detected | None detected |

While these chia seeds were relatively clean to start with, a significant reduction was observed for yeast, mold and Coliforms. All three types of microbes were reduced to below the detection threshold after treatment, confirming that a mist or atomized initial application of the treatment solution is effective to sanitize mucilaginous seeds in a large scale process.

Reaction Time 1 kg aliquots of cleaned, unprocessed hemp seeds were weighted into clean containers sterilized with 70% ethanol. Neo-Pure solution was prepared by dissolving Neo-Pure powder in tap water to a final concentration of 10% (w/v) and incubated at room temperature (RT) for 15 minutes to allow the formation of active peracetic acid (PAA) as the active ingredient. For some trials, ethanol was added to a final concentration of 50% (v/v) to generate a sanitizing solution containing 5% Neo-Pure (w/v) and 50% ethanol (v/v). 50 ml solution was applied to the seeds at a target application rate of 50 l/tonne with a small hand-held vaporizer. PAA activity was confirmed to be >160 ppm using test strips (LaMotte Insta-Test Analytic Peracetic Acid) during application. Post treatment, all aliquots were stored at room temperature in sealed containers until sampling.

Samples were taken 3 hours, 21 hours, 27 hours and 48 hours post treatment and plated on 3M Petrislides within 2 hours of sampling to determine total aerobic counts. Sample processing was conducted according to manufacturers recommendations. In brief, 7 g sample were added to 700 ml water and homogenized for 2 min using a handmixer. A dilution series was generated using sterile 9 ml buffered peptone water aliquots (3M) and 1 ml of the relevant dilutions were plated onto 3M Petrifilm Aerobic Count Plates. Petrifilms were incubated at 31° C. for 72 hours before counting. The total aerobic count (ACC) results for the samples are presented in FIG. 8. The UTC result is for untreated seed. "o/n" indicates samples taken at +21 hours, +24 indicates samples taken at 27 hours and +48 indicates samples taken at +48 hours.

Figure 8:
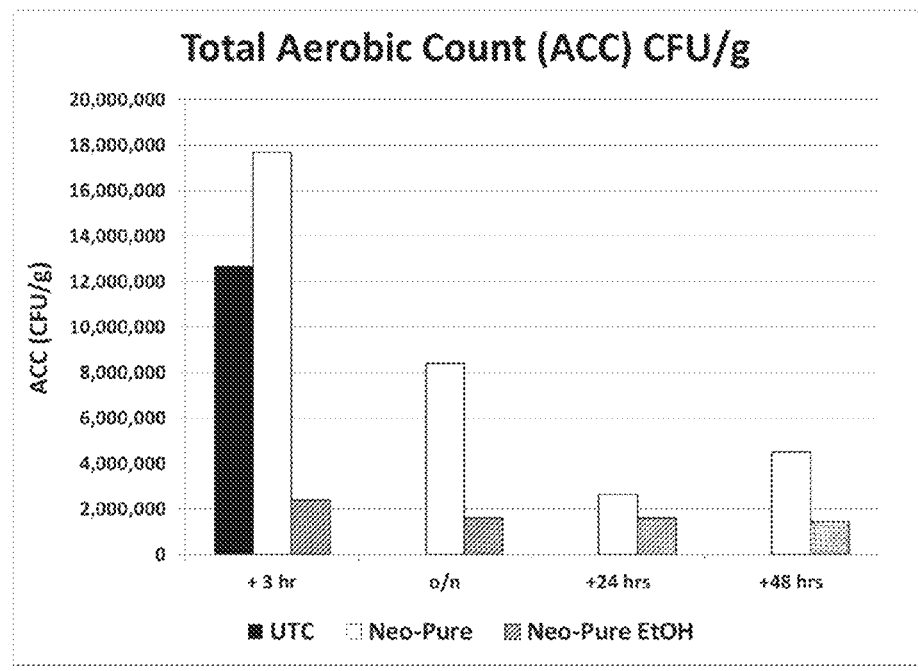
FIG. 8 is a graph of experimental results showing aerobic counts at various incubation times.

As indicated in FIG. 8, contact times longer than 3 hours have a beneficial effect on efficacy. However, there is an upper limit to the beneficial effect of longer contact time. With overly long contact times, microbial regrowth can occur. As described elsewhere in this patent, the contact time and threat of microbial regrowth are terminated by drying the treated seeds. The presence of ethanol not only enhanced efficacy of the treatment but also extended the time window where effective sanitization without microbial regrowth occurs.

The inventors believe that, under at least some circumstances, contact time could be increased beyond 48 hours, for example to 72 hours or more, without resulting in unacceptable microbial regrowth. However, since there was an indication that regrowth was starting in the non-ethanol formulation in FIG. 8 at 48 hours, and there was no trend towards increased efficacy with contact time past 27 hours, it would be preferable to restrict incubation time to 48 hours or less, or more preferably to 27 or 24 hours or less. In other trials described herein, adequate sanitizing effect was observed in at least some trials essentially on initial contact, where the incubation time might have been only in the range of 2-20 minutes. However, efficacy appears to increase with 3 hours or more of contact time and to an even greater extend with 21 hours or more of contact time. As described in other results presented further above, contact times of 12 and 24 hours were successfully used to sanitize seeds. Overall, a contact time of about 24 hours provides good results over a wide range of treatment solutions and seeds. A contact time range of 16-32 hours, or 21-27 hours, is expected to also provide good results while accommodating an ordinary work schedule. For example, the treatment solution is applied to the seeds and the seeds are transferred to holding containers on one day, and the seeds are removed from their holding containers and moved to a drier on the following day.

The examples and embodiments described herein are for illustrative purposes to help provide an enabling description of the invention. Various modifications or changes in light thereof will be suggested to persons skilled in the art.

We claim:

1. A method for sanitizing mucilaginous seeds comprising the steps of,
providing a sanitizing composition comprising water, at least one biocidal agent and at least one alcohol in an amount effective to suppress the release of mucilage from mucilaginous seeds;
applying a mist of the sanitizing composition to the mucilaginous seeds; and,
drying the seeds by forced air drying,
wherein the biocidal agent is selected from the group consisting of peracetic acid, hydrogen peroxide, iodine, chlorine, bromine and chlorine dioxide.

2. The method of claim 1 wherein the sanitizing composition is kept in contact with the mucilaginous seeds for at most 24 hours before drying the seeds.

3. The method of claim 1 wherein the sanitizing composition comprises at least 13% by volume of propylene glycol, or at least 15% by volume of ethanol, or a mixture of ethanol and propylene glycol comprising at a minimum concentration obtained by linear interpolation of the values for ethanol and propylene glycol.

4. The method of claim 1 wherein the sanitizing composition comprises between 15% and 20% ethanol by volume.

5. The method of claim 1 wherein the sanitizing composition comprises peracetic acid.

6. A method for sanitizing raw edible mucilagenous seeds comprising the steps of,
providing an aqueous sanitizing composition comprising at least one biocidal agent and at least 13% by volume of one or more alcohols;
applying a mist of the sanitizing composition to the mucilaginous seeds;
and,
drying the seeds,
wherein the biocidal agent is selected from the group consisting of peracetic acid, hydrogen peroxide, iodine, chlorine, bromine and chlorine dioxide.

7. The method of claim 6 wherein the sanitizing composition comprises at least 15% by volume of one or more alcohols.

8. The method of claim 6 wherein the sanitizing composition comprises at least 15% ethanol by volume.

9. The method of claim 6 wherein the applying step comprises spraying the sanitizing composition on the seeds followed by mixing the seeds.

10. The method of claim 6 comprising contacting the sanitizing composition with the seeds for at least 5 minutes, but not more than 24 hours, before drying the seeds.

11. The method of claim 6 wherein the sanitizing composition is applied at not more than 15% by weight of the seeds.

12. The method of claim 6 wherein in the drying step the seeds are dried to a water content of 10% or less relative to the weight of the seeds, or to a water content no more than 1% by weight of the seeds more than the water content of the seeds before applying the sanitizing composition to the seeds.

13. The method of claim 6 wherein the wherein the sanitizing composition comprises peracetic acid.

14. A sanitizing composition comprising,
water;
one or more biocidal agents; and,
one or more alcohols in an amount effective to suppress the release of mucilage from mucilaginous seeds,
wherein the one or more alcohols comprise ethanol, wherein the ethanol is present in an amount that is at least 15% by volume of the composition but does not exceed 20% by volume of the composition,
wherein the biocidal agents are selected from the group consisting of peracetic acid, hydrogen peroxide, iodine, chlorine, bromine and chlorine dioxide.

15. The sanitizing composition of claim 14 comprising peracetic acid.

16. The sanitizing composition of claim 14 comprising ethanol, propylene glycol, or both.

17. The sanitizing composition of claim 14 wherein the biocidal agent comprises one or more of peracetic acid and hydrogen peroxide.

18. The method of claim 1 wherein the sanitizing composition is in contact with the mucilaginous seeds for at least 5 minutes after applying the mist of the sanitizing composition to the mucilaginous seeds but before drying the seeds by forced air drying.

19. The method of claim 6 wherein the drying step comprises passing air through a bed of the seeds wherein the air is heated to not more than 70° C.

* * * * *